（12) United States Patent
Lentz et al.

(10) Patent No.: US 9,011,374 B2
(45) Date of Patent: Apr. 21, 2015

(54) BALLOON CATHETER WITH THREE LUMENS

(75) Inventors: David C. Lentz, Bloomington, IN (US); Christopher M. Mobley, Bloomington, IN (US); Peter A. Polverini, III, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 397 days.

(21) Appl. No.: 13/492,031

(22) Filed: Jun. 8, 2012

(65) Prior Publication Data

US 2012/0316436 A1    Dec. 13, 2012

Related U.S. Application Data

(60) Provisional application No. 61/495,595, filed on Jun. 10, 2011.

(51) Int. Cl.
| | | |
|---|---|---|
| *A61M 25/10* | (2013.01) | |
| *A61M 25/098* | (2006.01) | |
| *A61M 25/00* | (2006.01) | |
| *A61M 25/01* | (2006.01) | |
| *A61F 2/954* | (2013.01) | |
| *A61F 2/958* | (2013.01) | |

(52) U.S. Cl.
CPC ......... *A61M 25/104* (2013.01); *A61M 25/0012* (2013.01); *A61M 25/0026* (2013.01); *A61M 25/0043* (2013.01); *A61M 25/0045* (2013.01); *A61M 25/0052* (2013.01); *A61M 25/0108* (2013.01); *A61M 25/1036* (2013.01); *A61M 2025/0059* (2013.01); *A61M 2025/0183* (2013.01); *A61M 2025/1052* (2013.01); *A61M 2025/1079* (2013.01); *A61F 2/954* (2013.01); *A61F 2/958* (2013.01)

(58) Field of Classification Search
USPC ............ 604/96.01, 102.01–102.03, 509–510, 604/522, 528–529; 606/192, 194, 200
See application file for complete search history.

(56) References Cited

U.S. PATENT DOCUMENTS

| | | | |
|---|---|---|---|
| 5,059,177 A | 10/1991 | Towne et al. | |
| 5,122,115 A | 6/1992 | Marks | |
| 5,569,184 A * | 10/1996 | Crocker et al. | ............... 604/509 |
| 5,637,086 A * | 6/1997 | Ferguson et al. | ............. 604/509 |
| 5,728,068 A | 3/1998 | Leone et al. | |
| 5,840,066 A * | 11/1998 | Matsuda et al. | ......... 604/102.02 |
| 6,517,533 B1 | 2/2003 | Swaminathan | |
| 6,702,781 B1 | 3/2004 | Reifart et al. | |
| 7,481,800 B2 | 1/2009 | Jacques | |
| 2003/0130610 A1 | 7/2003 | Mager et al. | |
| 2005/0113798 A1 | 5/2005 | Slater et al. | |
| 2006/0195136 A1 | 8/2006 | Yokoyama et al. | |
| 2008/0091067 A1 | 4/2008 | Dollar | |

FOREIGN PATENT DOCUMENTS

WO    WO 2009036135 A1 *    3/2009

* cited by examiner

*Primary Examiner* — Theodore Stigell
*Assistant Examiner* — Amber Stiles
(74) *Attorney, Agent, or Firm* — Brinks Gilson & Lione (57) ABSTRACT

A balloon catheter is provided with three lumens. The first lumen may be used as a guide wire lumen. The second lumen may be used as an inflation lumen. The third lumen may be used to provide various treatments to a vessel. Methods of using the balloon catheter to treat a patient are also provided.

26 Claims, 6 Drawing Sheets

BALLOON CATHETER WITH THREE LUMENS

This application claims priority to U.S. Provisional Application No. 61/495,595, filed Jun. 10, 2011, which is hereby incorporated by reference herein.

BACKGROUND

The present invention relates generally to medical devices and more particularly to intraluminal balloon catheters.

Balloon catheters are widely used in the medical profession for various intraluminal procedures. One common procedure involving the use of a balloon catheter relates to angioplasty dilation of coronary and other arteries suffering from stenosis (i.e., a narrowing of the arterial lumen that restricts blood flow). Angioplasty procedures have become a popular alternative to traditional procedures for treating stenoses because angioplasty procedures are considerably less invasive than other alternatives. For example, stenosis of the coronary arteries has traditionally been treated by performing bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. Angioplasty procedures are also useful for treating stenoses in other regions of the vasculature as well, such as the carotid, brachial, renal, iliac and femoral arteries. In addition, angioplasty may be used to treat other vessels and passageways in the body.

Typically, angioplasty procedures are performed using a balloon-tipped catheter that may or may not have a balloon-expandable stent mounted on the balloon. In general, a physician performs an angioplasty procedure by introducing a balloon catheter into a peripheral artery (commonly one of the leg or arm arteries) and threading the catheter to the narrowed region of the artery. During this stage, the balloon is uninflated and collapsed onto the shaft of the catheter in order to present a low profile which may be passed through the arterial lumens. Once the balloon is positioned at the narrowed region of the artery, the balloon is expanded by pumping a mixture of saline and contrast solution through the catheter to the balloon. As a result, the balloon presses against the inner wall of the artery to dilate it. If a balloon-expandable stent is mounted on the balloon, the balloon inflation also serves to expand the stent and implant it in the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. Alternatively, the balloon catheter may be used to dilate a stenosis without implanting a stent. A balloon-expandable stent or self-expandable stent may then be implanted in the dilated region in a follow-up procedure. If desired, a physician may also dilate the artery and stent a second time after the stent is implanted with a balloon catheter.

Although treatment of stenosed arteries in the vasculature is one common example where balloon catheters are used, this is only one example of how balloon catheters may be used and many other uses are possible. For example, balloon catheters may also be used to temporarily occlude vessels during medical procedures to prevent blood or other fluids from flowing through a vessel. Balloon catheters may also be used to expand other intraluminal devices without dilating the surrounding vessel wall, such as stent-grafts that may be used to treat aneurysms.

The above-described examples are only some of the applications in which balloon catheters are used by physicians. Many other applications for balloon catheters are known and/or may be developed in the future.

SUMMARY

A balloon catheter is described which may be used to provide several different medical treatments. The balloon catheter has three lumens. One lumen may be a guide wire lumen. Another lumen may be an inflation lumen for the balloon. The third lumen has an opening located proximally from the balloon. Various solutions and devices may be passed through the third lumen and out the opening of the third lumen to provide treatments to the vessel. The lumens may also be made with thin-walled high strength liners. The invention may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1A:
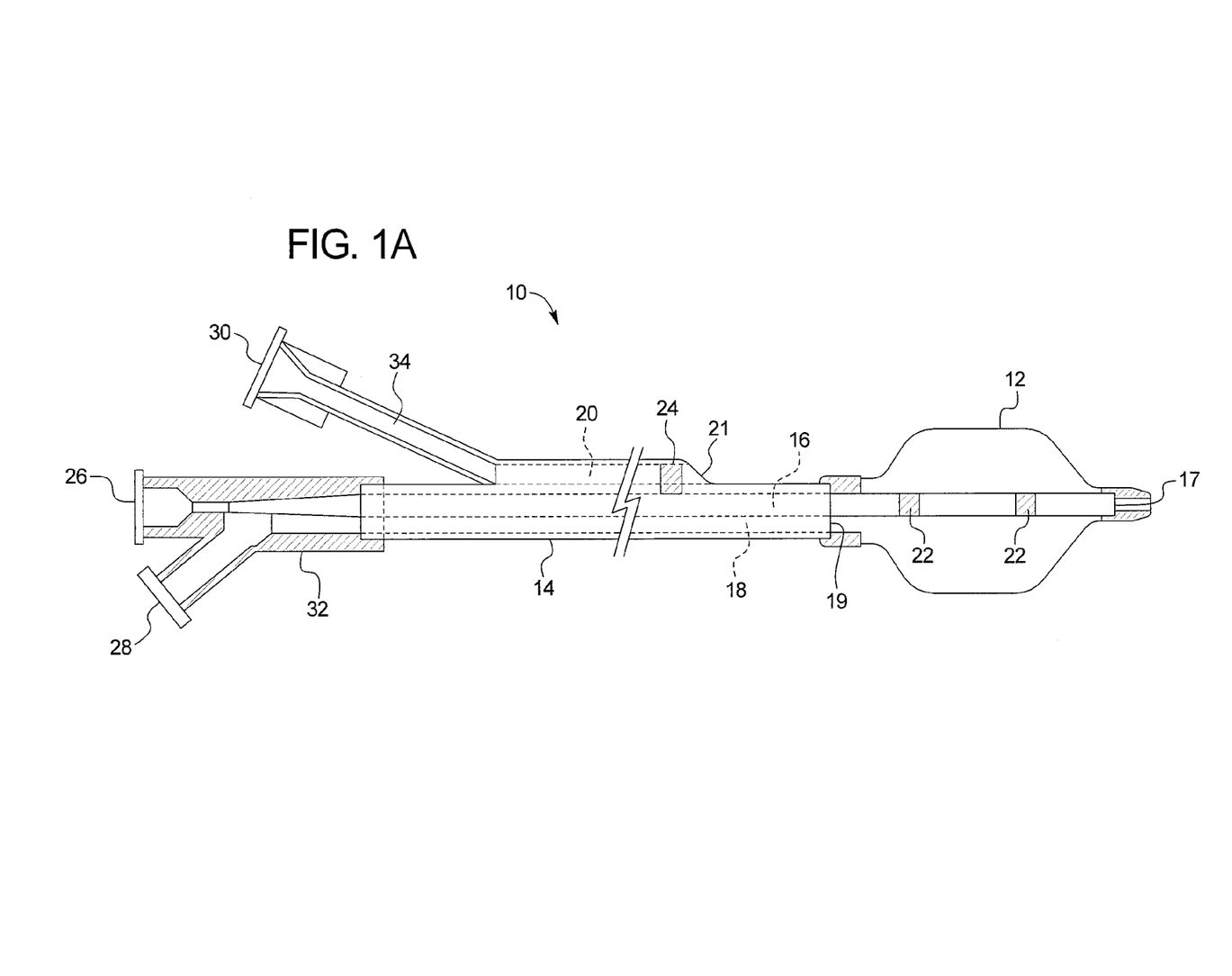
FIG. 1A is a side view of a balloon catheter.

Referring now to the figures, and particularly to FIG. 1A, a balloon catheter 10 is shown. The balloon catheter 10 is provided with a balloon 12 at the distal end of the balloon catheter 10. The balloon 12 is conventional in nature and may be non-compliant, semi-compliant or compliant. A typical material that may be used for the balloon 12 is nylon. The balloon 12 is attached to the distal end of a catheter shaft 14, so that the proximal end of the catheter shaft 14 is intended to remain outside of a patient's body during the medical treatment for manipulation by a physician, and the distal end is intended to be inserted into the patient's body for medical treatment.

The catheter shaft 14 has three lumens 16, 18, 20 extending from the proximal end to the distal end. The first lumen 16 extends through the catheter shaft 14 and the inner cavity of the balloon 12 to the most distal portion of the balloon catheter 10. A first opening 17 is provided at the distal end of the first lumen 16 so that the first lumen 16 can be used as a guide wire lumen 16. The second lumen 18 extends through the catheter shaft 14 to a location near the proximal side of the balloon 12. A second opening 19 is provided at the distal end of the second lumen 18 within the inner cavity of the balloon 12 so that an inflation media can flow through the second lumen 18 to inflate and deflate the balloon 12. The third lumen 20 extends through the catheter shaft 14 to a location proximal from the balloon 12. A third opening 21 is provided at the distal end of the third lumen 20 approximately 5 mm to 10 mm from the proximal end of the balloon 12, where the proximal end is considered to be where the tapered portion of the balloon 12 meets the neck of the balloon 12. The third opening 21 communicates with the exterior region around the catheter shaft 14 proximal from the balloon 12. As further described below, the third lumen 20 may be used in various medical treatments. Although the cross-section of the first, second and third lumens 16, 18, 20 may vary depending upon the particular application that the balloon catheter 10 is designed for, in one exemplary embodiment, the inner diameter of the first lumen 16 may be about 0.015" to about 0.018"; the inner diameter of the second lumen 18 may be about 0.016" to about 0.021"; and the inner diameter of the third lumen 20 may be about 0.012" to about 0.025".

First radiopaque bands 22 may be provided on the outside of the first lumen 16 within the inner cavity of the balloon 12. Thus, in use, the first radiopaque bands 22 provide an indication of the location of the balloon 12 within a patient's body. A second radiopaque band 24 may also be provided adjacent the third opening 21 of the third lumen 20. Thus, in use, the second radiopaque band 24 provides indications of both the longitudinal position of the third opening 21 and the radial orientation of the third opening 21 within the patient's body.

Figure 1B:
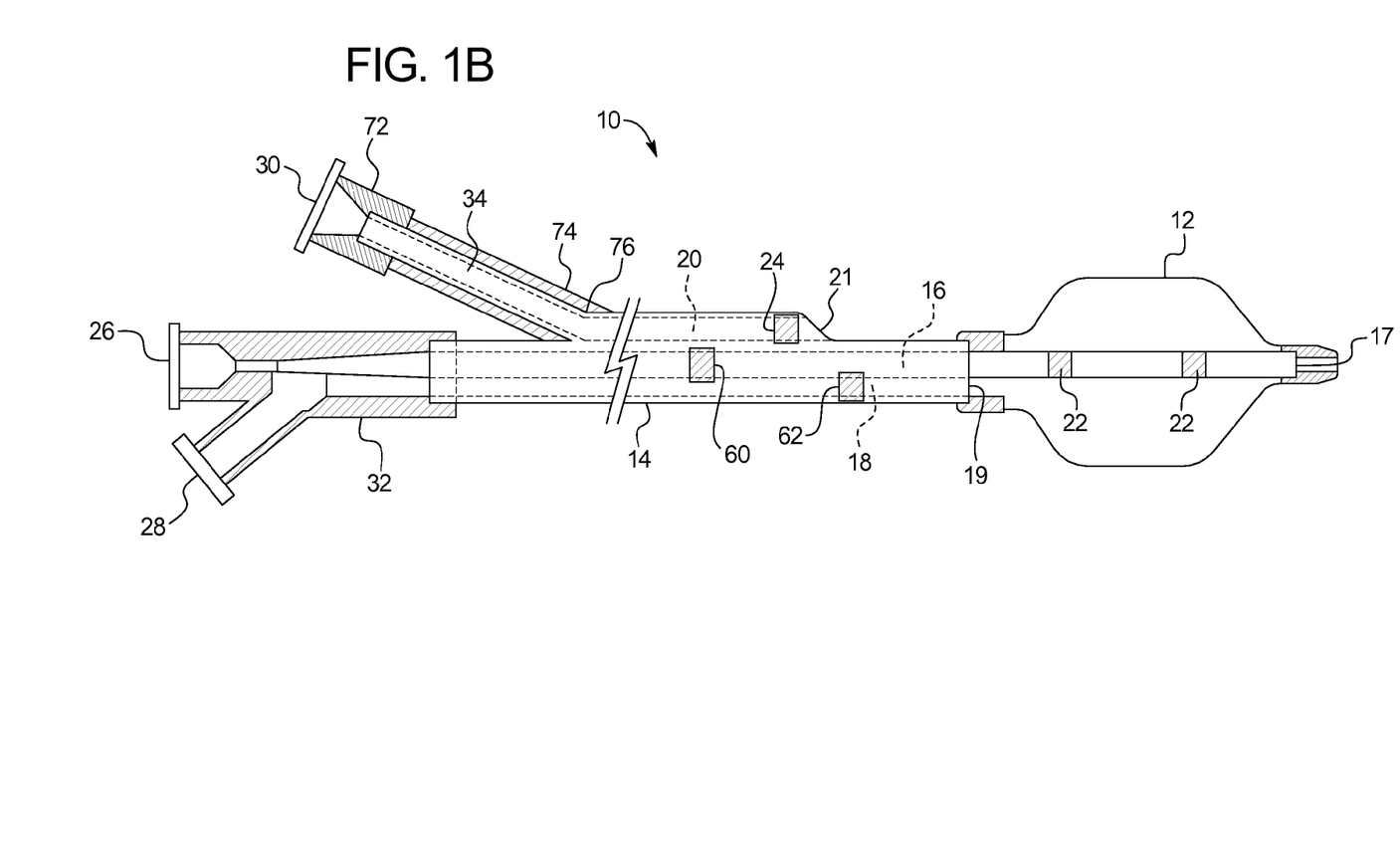
FIG. 1B is a side view of another balloon catheter.

As shown in FIG. 1B, third and fourth radiopaque bands 60, 62 may also be provided around the first lumen 16 and second lumen 18 adjacent the second radiopaque band 24. For example, the third radiopaque band 60 may be provided on the first lumen 16 proximally adjacent the second radiopaque band 24, and the fourth radiopaque band 62 may be provided on the second lumen 18 distally adjacent the second radiopaque band 24. The third and fourth radiopaque bands 60, 62 could also be reversed in order if desired, or one of the third and fourth radiopaque bands 60, 62 could adjacent a radiopaque band 60, 62 that is adjacent the second radiopaque band 24. This staggered arrangement of the second, third and fourth radiopaque bands 24, 60, 62 may be useful in providing an improved indication of radial orientation of the third opening 21 within the patient's body.

The first, second and third lumens 16, 18, 20 communicate with corresponding first, second and third ports 26, 28, 30 at the proximal end of the catheter shaft 14. Preferably, the first port 26 is axially aligned with the first lumen 16 so that a guide wire inserted through the first lumen 16 remains straight as it passes through the first port 26 into the first lumen 16. The second port 28 may be angled from the second lumen 18, and the angle is relatively inconsequential since only inflation media passes through the second port 28 and second lumen 18. Preferably, the first and second ports 26, 28 are integrally formed together at a single Y-shaped hub 32.

A separate extension lumen 34 preferably extends between the third port 30 and the third lumen 20. Because various types of medical instruments may be inserted into the third lumen 20, it is preferred that the non-included angle between the extension lumen 34 and the third lumen 20 is minimized to reduce the amount of bending that is required of medical instruments as they pass through the extension lumen 34 into the third lumen 20. For example, in one embodiment, the extension lumen 34 may be defined by a stiff material that maintains a constant angular relationship with the third lumen 20. In this embodiment, the non-included angle between the extension lumen 34 and the third lumen 20 is preferably 30° or less. In another embodiment, the extension lumen 34 may be defined by a soft material that is flexible and movable relative to the third lumen 20. In this embodiment, the non-included angle may be adjustable by the physician to suit a particular medical instrument being passed through the extension lumen 34 and third lumen 20. In order to minimize the angle between the extension lumen 34 and the third lumen 20, the junction between the extension lumen 34 and the third lumen 20 is preferably distal from the Y-shaped hub 32 of the first and second ports 26, 28. Thus, the third lumen 20 may terminate distally from the proximal ends of the first and second lumens 16, 18.

Turning to FIGS. 2A-2G, the first, second and third lumens 16, 18, 20 may each be defined by a thin-walled liner 36, 38, 40 made of a high-strength material. However, depending upon the particular application that the balloon catheter 10 is designed for, only one or two of the first, second and third lumens 16, 18, 20 may be made from a thin-walled high strength material. For example, it may not be necessary to make the first lumen 16 from a thin-walled high strength material when the first lumen 16 is primarily intended as a guide wire lumen 16. However, it may be preferable to make the second lumen 18 from a thin-walled high strength material to increase the burst pressure of the second lumen 18 to allow higher inflation pressures in the balloon 12. It may also be preferable to make the third lumen 20 from a thin-walled high strength material to increase the burst pressure of the third lumen 20 and to stiffen the catheter shaft 14.

For example, the thin-walled liners 36, 38, 40 of the first, second or third lumens 16, 18, 20 may be made of a polyimide or PTFE. Where the thin-walled liners 36, 38, 40 are made from PTFE, it is preferable to use etched PTFE, which enables the outer surface of the thin-walled liner 36, 38, 40 to be heat bonded to the catheter shaft 14. While PTFE is a high-strength material, it is relatively flexible. Thus, PTFE may be preferred where a flexible catheter shaft 14 is desired. Preferably, the wall thickness of a PTFE liner is about 0.0008" to about 0.002". Where the thin-walled liners 36, 38, 40 are made from polyimide, it is preferable to use thermoset polyimide. Because thermoset polyimide is relatively stiff, thermoset polyimide may be preferred where a stiffer catheter shaft 14 is desired. Because thermoset polyimide is not easily heat bondable, it is preferred in the embodiment where thermoset polyimide is used that the thin-walled liner 36, 38, 40 be a dual layer liner with thermoset polyimide being the inner layer and a thermoplastic, such as polyamide, being the outer layer. Preferably, the wall thickness of a thermoset polyimide liner is about 0.0006" to about 0.0017" for the polyimide layer and about 0.0002" to about 0.0005" for the thermoplastic layer.

Figure 2A:
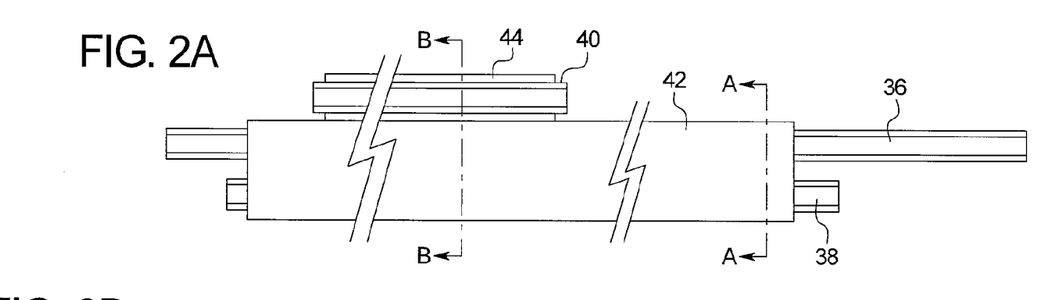
FIG. 2A is a side view of the catheter shaft before melt reflow.
Figure 2B:
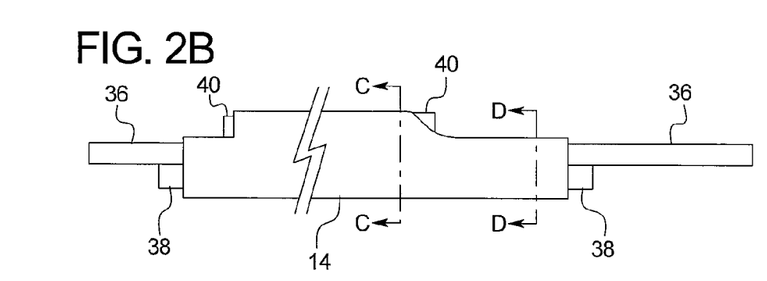
FIG. 2B is a side view of the catheter shaft after melt reflow.
Figure 2C:
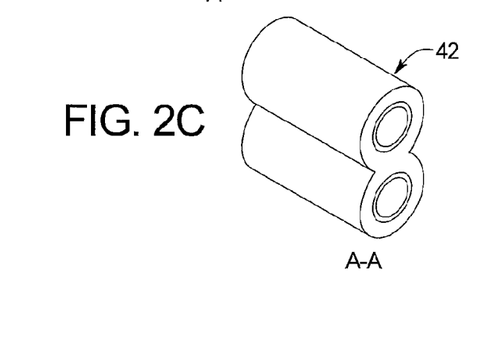
FIG. 2C is perspective view of a figure 8-shaped thermoplastic extrusion.
Figure 2D:
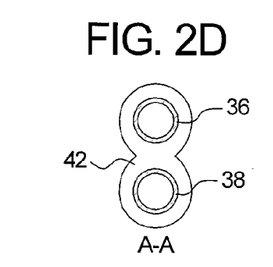
FIG. 2D is a cross-sectional view along section A-A in FIG. 2A.
Figure 2E:
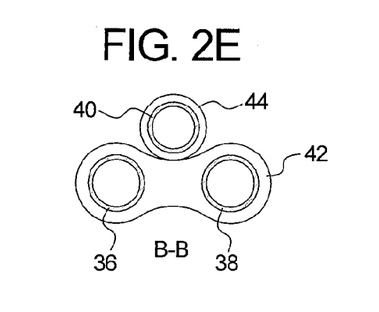
FIG. 2E is a cross-sectional view along section B-B in FIG. 2A.
Figure 2F:
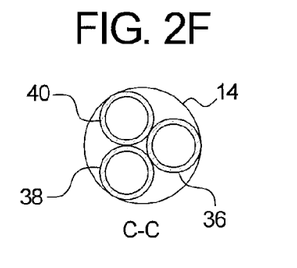
FIG. 2F is a cross-sectional view along section C-C in FIG. 2B.
Figure 2G:
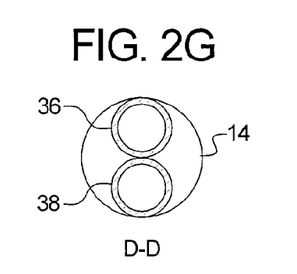
FIG. 2G is a cross-sectional view along section D-D in FIG. 2B.

As shown in FIG. 2A, the liners 36, 38, 40 for the first, second and third lumens 16, 18, 20 may be inserted into thermoplastic extrusions 42, 44. A material that is readily adapted for melt reflow is preferred for the extrusions 42, 44, such as an amide based polymer like nylon, polyurethane or PEBA. As shown in FIGS. 2C and 2D, the liners 36, 38 for the first and second lumens 16, 18 may be inserted into a FIG. 8-*shaped* extrusion 42. As shown in FIG. 2E, the liner 40 for the third lumen 20 may be inserted into a separate single lumen extrusion 44. However, it is possible that other types of extrusions may be used. For example, an extrusion with three lumens for each of the liners 36, 38, 40 could also be used. After the liners 36, 38, 40 are inserted into the extrusions 42, 44, the extrusions 42, 44 are placed within one or more lengths of heat shrink tubing. The entire assembly is then heated to cause the thermoplastic materials to melt together and cause the heat shrink tubing to squeeze the entire assembly together into a compact cross-section. Once the catheter shaft 14 has been formed as desired, the catheter shaft 14 may be cooled and the heat shrink tubing removed. As shown in FIGS. 2F and 2G, the finished cross-sections of the catheter shaft 14 are generally round. However, the overall profile of the catheter shaft 14 along the third lumen 20, as shown in FIG. 2F, may be larger than the profile of the portion without the third lumen 20, as shown in FIG. 2G. As also shown in FIGS. 2F and 2G, the wall thicknesses between the outer surface of the catheter shaft 14 and the first, second and third lumens 16, 18, 20 may be especially thin along the outer wall portions. However, where thin-walled high strength liners 36, 38, 40 are used for the lumens 16, 18, 20, the liners 36, 38, 40 may maintain integrity of the catheter shaft 14 despite the thin outer wall portions.

Referring back to FIG. 1B, it may be preferable for the extension lumen 34 to be made from the same thin-walled liner 40 that defines the third lumen 20. That is, the liner 40 for the third lumen 20 may be angled away from the liners 36, 38 for the first and second lumens 16, 18 near the Y-shaped hub 32 for the first and second ports 26, 28. Thus, there is no joint between the liner 40 and a separate tube where the extension lumen 34 branches from the first and second lumens 16, 18. Instead, the liner 40 extends through the extension transition 76 all the way to a hub 72 that is bonded onto the end of the liner 40. To avoid kinking the liner 40, it is preferable for the non-included angle between the extension lumen 34 and the third lumen 20 to be 30° or less. An advantage of this design is that the third lumen 20 may be able to withstand higher pressures without bursting the wall of the extension lumen 34 or the transition 76 between the third lumen 20 and the extension lumen 34. Since the liner 40 is preferably made of polyimide or PTFE as described above, the liner 40 may provide a higher burst pressure along the extension lumen 34 compared to conventional materials that could be used for the extension lumen 34. However, because the liner 40 is relatively thin, the liner 40 may not be able to rigidly maintain the branched shape of the extension lumen 34 by itself. Thus, it may be desirable to provide a reinforcement outer layer 74 along the length of the extension lumen 34 to support the liner 40. The reinforcement layer 74 may be made from a thermoplastic that is melted around the liner 40 as described above.

Figure 3A:
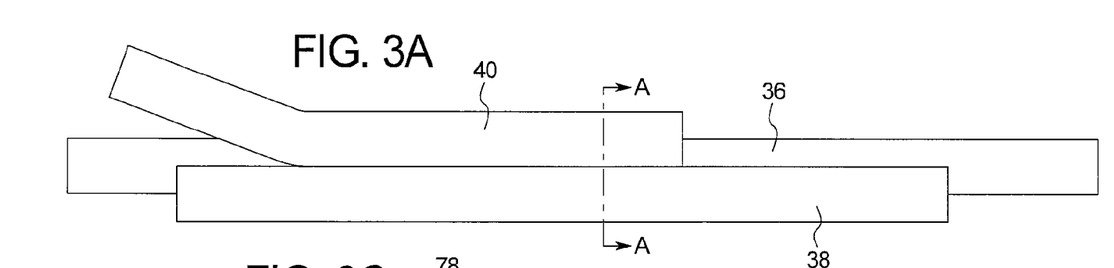
FIG. 3A is a side view of three liners positioned adjacent each other.
Figure 3B:
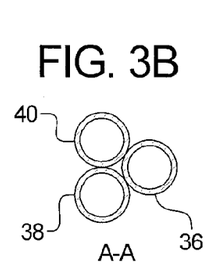
FIG. 3B is a cross-sectional view along section A-A in FIG. 3A.
Figure 3C:
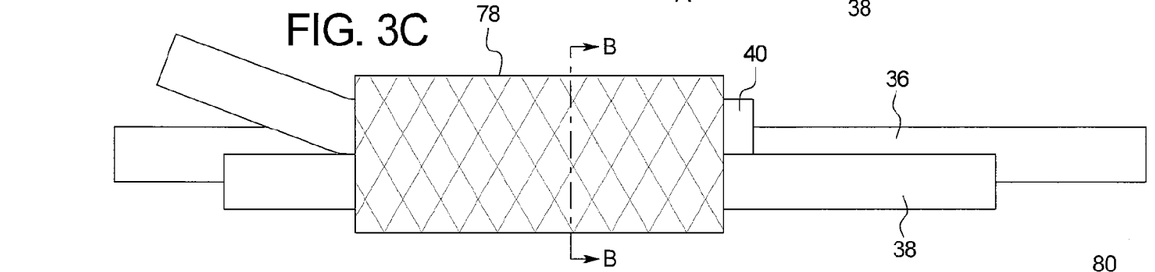
FIG. 3C is a side view of a braided reinforcement structure disposed around the three liners.
Figure 3D:
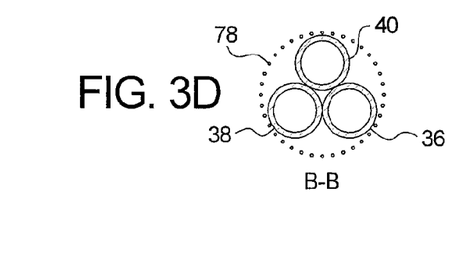
FIG. 3D is a cross-sectional view along section B-B in FIG. 3C.
Figure 3E:
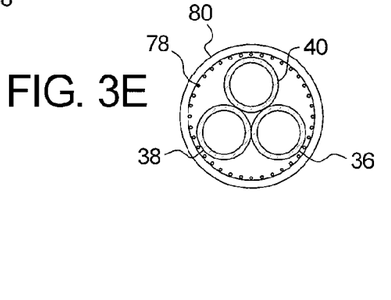
FIG. 3E is a cross-sectional view of a thermoplastic tube disposed around the braided reinforcement structure.
Figure 3F:
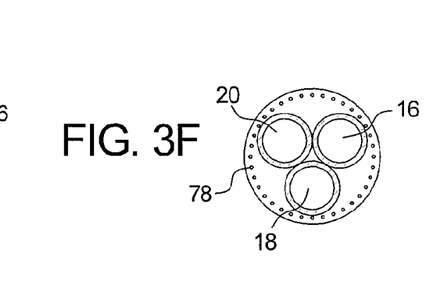
FIG. 3F is a cross-sectional view of the structure of FIG. 3E after melt reflow.

As shown in FIGS. 3A-3F, it may be preferable to include a braided reinforcement structure 78, such as a metallic braid 78, along a length of the first, second and third lumens 16, 18, 20 without covering the third opening 21. The braided reinforcement structure 78 may be useful in improving the torqueability of the balloon catheter 10 so that the third opening 21 of the third lumen 20 can be rotationally oriented within the patient's body as desired. The balloon catheter 10 with a braided reinforcement structure 78 may be made using similar steps described above with respect to FIGS. 2A-2G. For example, in FIG. 3A, the liners 36, 38, 40 may be positioned next to each other so that the liners 36, 38, 40 are in a triangular relationship as shown in FIG. 3B. As shown in FIGS. 3C-3D, a braided reinforcement structure 78 may then be slid over the three liners 36, 38, 40. As shown in FIG. 3E, a thermoplastic tube 80 may then be slid over the braided reinforcement structure 78. As shown in FIG. 3F, the thermoplastic tube 80 may then be melted so that the thermoplastic material 80 penetrates through the braided reinforcement structure 78 and bonds to the liners 36, 38, 40. This may be accomplished using heat shrink tubing as described above.

Figure 4A:
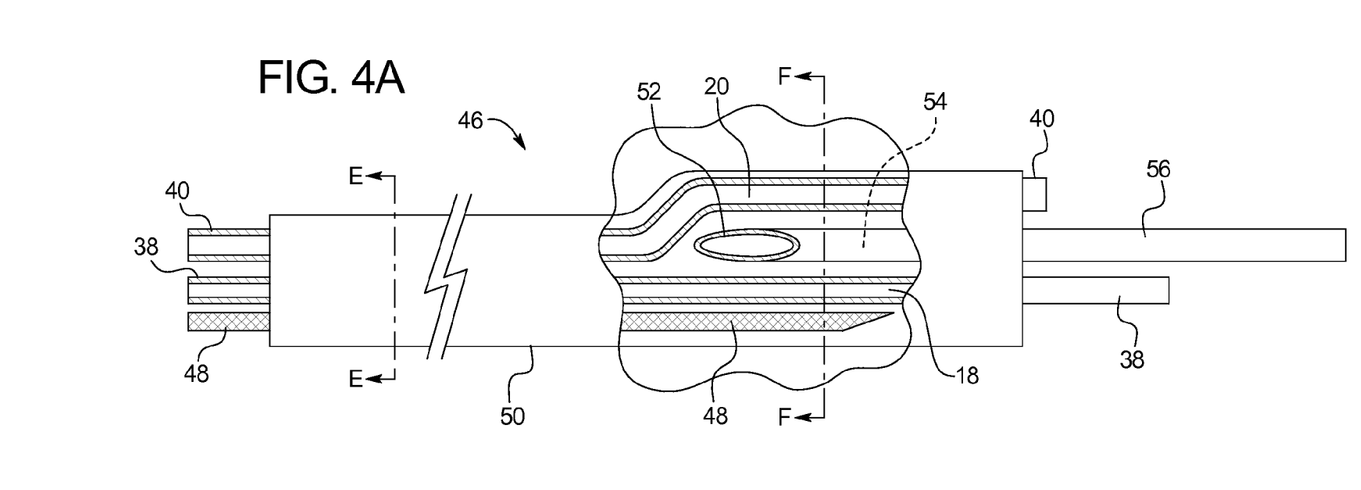
FIG. 4A is a side view of a catheter shaft for a rapid exchange balloon catheter.
Figure 4B:
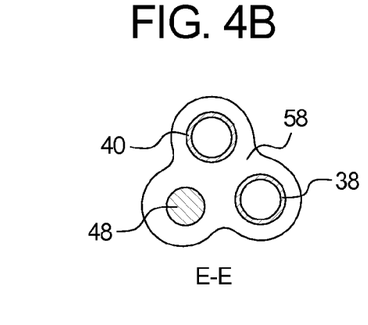
FIG. 4B is a cross-sectional view along section E-E in FIG. 3A before melt reflow.
Figure 4C:
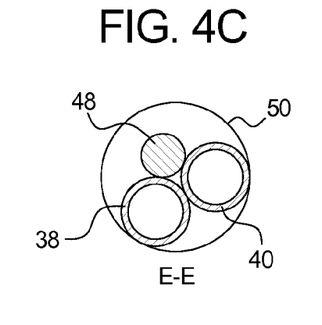
FIG. 4C is a cross-sectional view along section E-E in FIG. 3A after melt reflow.
Figure 4D:
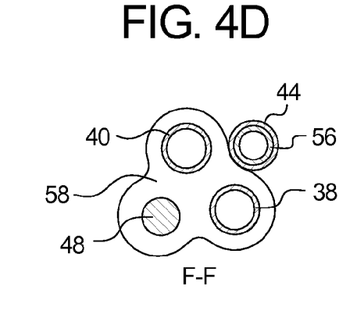
FIG. 4D is a cross-sectional view along section F-F in FIG. 3A before melt reflow.
Figure 4E:
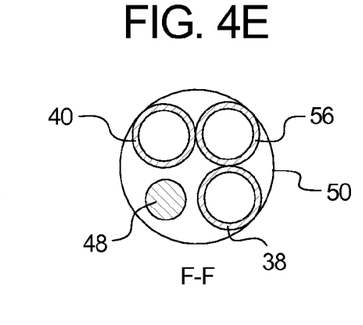
FIG. 4E is a cross-sectional view along section F-F in FIG. 3A after melt reflow.

Turning to FIGS. 4A-4E, the balloon catheter 46 may also be designed as a rapid exchange balloon catheter 46. Thus, in addition to the features described above, a stiffening mandrel 48 may also be provided along the proximal portion of the catheter shaft 50. Another difference in the rapid exchange balloon catheter 46 is that the first port 52 for the first lumen 54 is not located near the proximal end of the catheter shaft 50, and instead is located at an intermediate location along the catheter shaft 50 which is intended to be inserted into a patient's body. While the third lumen 20 is shown contoured around the first port 52 of the first lumen 54 in FIG. 4A, this is shown for illustration purposes, and it is preferable for the third lumen 20 to remain straight along its length. As shown in FIGS. 4B and 4D, the stiffening mandrel 48 and the first, second and third liners 56, 38, 40 may be inserted into thermoplastic extrusions 58, 44 as described above. However, in this embodiment, the first liner 56 may be inserted into a single lumen extrusion 44. As further shown FIGS. 4C and 4D, heat shrink tubing may be used to heat bond the catheter shaft 50 into a low profile generally round cross-section.

Preferably, the proximal ports 26, 28, 30 and the balloon 12 are attached to the catheter shaft 14 after the thermoplastic extrusions 42, 44, 58 have been heat bonded to the liners 36, 38, 40, 56. The balloon 12 may be attached to the distal end of the catheter shaft 14, 50 using melt reflow in a similar way that the catheter shaft 14, 50 is formed. For example, heat shrink tubing may be placed over the proximal and distal necks of the balloon 12 to bond the distal neck to the first liner 36, 56 and the proximal neck to the body of the catheter shaft 14, 50 over the first and second liners 36, 38, 56. The Y-shaped hub 32 and the extension lumen 34 and third port 30 may be attached to the proximal end of the catheter shaft 14, 50 by melt reflow or adhesives.

Embodiments of the balloon catheter 10, 46 may be used in a variety of medical treatments. For example, in one medical treatment, the balloon catheter 10, 46 is inserted through a patient's vessel using conventional techniques and positioned so that the balloon 12 extends through a stenosis. The balloon 12 is then inflated at the stenosis to dilate the stenosis. After the balloon 12 has been inflated in an effort to open the stenosis, the balloon 12 is deflated but is not immediately withdrawn from the treatment site. While the deflated balloon 12 remains at the treatment site, contrast solution is injected through the third lumen 20 of the balloon catheter 10, 46 so that it exits the third opening 21 proximal from the balloon 12. The physician may then use visualization equipment to view the treatment site to determine the effect of the first balloon dilation. If the physician determines that further dilation of the stenosed region is desirable, the physician can inflate the balloon 12 a second time to dilate the stenosed region again without moving the balloon 12 between the first and second dilations.

One advantage of this method of treating a stenosis is that the overall time to treat a stenosis can be reduced. For example, in conventional treatment methods, the deflated balloon is typically either fully removed from the patient's body after the first dilation or is partially withdrawn into a guide catheter. This is considered desirable in conventional techniques because sufficient contrast solution cannot be injected through the annular space between a conventional balloon catheter and the guide catheter when the balloon catheter is located at the stenosis. However, if a second dilation is required, the conventional balloon catheter must be repositioned at the stenosis, which increases the overall time of the procedure. The practice of repositioning a conventional balloon catheter at a stenosis for a second dilation also has other problems in addition to requiring more time for the procedure. For example, if the balloon catheter is fully removed from the patient's body, the balloon catheter may become contaminated while it is outside the patient's body. To avoid this risk, the physician may choose to use a new balloon catheter for the second dilation, but this increases the cost of the procedure. In addition, even if the conventional balloon catheter is only partially withdrawn, it can be difficult to precisely reposition the balloon catheter at the exact same position where it was located during the first dilation. As a result, it is possible that that the conventional balloon may be at a slightly different position during the second dilation, which can result in undilated tissue being unnecessarily dilated and damaged during the second dilation. These problems are overcome with the balloon catheter 10, 46 and procedure described because the balloon 12 is not substantially moved between the first and second dilations.

Another advantage of the improved method is that less contrast solution and better visualization of the stenosed region may be possible. Contrast solution is potentially toxic for certain patients at certain dosages. Thus, in general, it is desirable to reduce the amount of contrast solution that is used. However, high quality visualization of the treatment site is also desirable to improve the results of the procedure. In the method described above, contrast solution is released into the vessel from the third opening 21 in close proximity to the stenosed region. For example, in the preferred embodiment of the balloon catheter 10, 46, the third opening 21 may be about 5 mm to about 10 mm from the proximal end of the balloon 12. However, it may also be desirable for the third opening 21 to be about 10 mm to about 50 mm from the proximal end of the balloon 12. Moreover, the contrast solution flows through the stenosis between the annular space between the stenosis and the deflated balloon 12. Thus, the space which must be filled with contrast solution to provide good visualization can be relatively small. By contrast, in conventional procedures, contrast solution is injected through a guide catheter and exits the distal opening of the guide catheter. However, the distal end of the guide catheter oftentimes is not located particularly close to the stenosed region. Thus, a larger length of the vessel is exposed to contrast solution and some of the contrast solution may pass through branch vessels that lead away from the stenosed region. In addition, the contrast solution in the conventional procedure flows through the entire cross-sectional space of the vessel. Therefore, it may be possible to achieve visualization quality from the improved procedure that is comparable to conventional procedures while using less contrast solution.

In addition, contrast solution may be injected through the balloon catheter 10, 46 at higher pressures than with conventional systems. In particular, conventional systems are limited because guide catheters typically have hemostatic valves at their proximal end to allow the insertion of medical devices therethrough, such as a conventional balloon catheter. As a result, the hemostatic valve can limit the pressure that is possible through the guide catheter, since high pressure injection can cause contrast solution to escape through the hemostatic valve. Moreover, guide catheters are typically made from flexible materials, which can limit the burst pressure of a guide catheter. However, in the balloon catheter 10, 46 described above, a pressure injector can be connected directly to the third port 30 in communication with the third lumen 20 and third opening 21 without the need for a hemostatic valve. Thus, there is no hemostatic valve to limit the pressure possible through the third lumen 20. In addition, by using a thin-walled high strength liner 40 for the third lumen 20, the burst pressure of the third lumen 20 can be increased.

In another medical treatment, drugs may be injected through the third lumen 20 and out the third opening 21 to treat the treatment site. This may be particularly useful where the treatment site is a stenosis and the vessel wall spasms after the first dilation. In this case, a drug such as nitroglycerin and/or pavpaverine may be injected through the third lumen 20 to treat the vessel spasm without substantially moving the balloon 12 from the stenosed region. This method has many of the advantages discussed above. For example, less drug may be needed since the drug is released close to the dilated region, and the drug is localized in the dilated region since it flows through the annular space between the dilated vessel wall and the deflated balloon 12. This method also reduces the number of medical instruments that may be used, reduces the overall time of the procedure, and allows the stenosed region to be easily dilated a second time after the drug is injected. Additionally, the methods described herein, both above and below, may be combined to achieve further benefits. For example, after the stenosed region has been dilated with the balloon 12 the first time, contrast solution may be injected to visualize the results of the first dilation. If it is determined that the vessel has spasmed, a drug can then be injected through the third lumen 20. The stenosed region can then be dilated a second time. As described, all of these steps can be performed without substantially moving the balloon 12 from the stenosed region.

In another medical treatment, a dilation wire may be inserted through the third lumen 20 so that it exits the third opening 21 and extends between the balloon 12 and a stenosed region. The balloon 12 may then be inflated to squeeze the dilation wire between the balloon 12 and the stenosed region. This may be particularly useful with stenosed regions that are calcified or especially hardened, since the dilation wire focuses the dilation pressure of the balloon 12 onto a narrow region which can result in cracking of a hardened stenosis. As explained above, this method may have several benefits. For example, the balloon 12 may be used to dilate a stenosed region a first time without the dilation wire. The method may then be combined with any of the other methods described herein. For example, contrast solution may be injected through the third lumen 20 to visualize the results of the first dilation. The dilation wire may then be inserted to dilate the stenosis a second time with the added force of the dilation wire. As described, all of these steps can be performed without substantially moving the balloon 12 from the stenosed region.

In another medical treatment, the balloon catheter 10, 46 may be used to treat an aneurysm. In this method, it is preferable for a compliant balloon 12 to be used, whereas a semi-compliant or non-compliant balloon 12 is preferred for treating a stenosis. The balloon 12 may be inflated slightly distally of the aneurysm so that the third opening 21 is located adjacent the aneurysm. An embolization coil can then be pushed through the third lumen 20 and out the third opening 21 into the aneurysm. The balloon catheter 10, 46 offers several advantages in this method because the balloon 12 serves to anchor the balloon catheter 10, 46 within the vasculature to prevent the third opening 21 from inadvertently moving away from the aneurysm while the embolization coil is being inserted into the aneurysm. In addition, the balloon 12 blocks the embolization coil from escaping the aneurysm and prevents the embolization coil from passing further down the vasculature. The balloon 12 may also be used to seat the embolization coil after it has been released from the third opening 21 by slightly deflating the balloon 12 and withdrawing it across the aneurysm. The balloon 12 may also be re-inflated at the aneurysm to further seat the embolization coil. Again, this method may be combined with the other methods described herein to achieve further advantages. For example, contrast solution may be injected through the third lumen 20 to visualize the aneurysm. This may be particularly useful when the balloon 12 is inflated, since the contrast solution will be trapped within the aneurysm region. As a result, the embolization coil could be inserted into the aneurysm while the contrast solution is trapped in the aneurysm region, which would provide the physician with real-time visualization. Another advantage of this method is that if the procedure requires a significant amount of time to complete or is performed in particularly sensitive areas, the balloon 12 could be intermittently deflated to allow blood to flow through so that the downstream tissues are not starved. The balloon 12 may then be re-inflated to continue the procedure.

In another medical treatment, the balloon catheter 10, 46 may be used to treat vessels that have been substantially occluded so that a guide wire and conventional balloon cannot pass through the occlusion. In this situation, physicians conventionally pass a guide wire and conventional balloon around the occlusion through the arterial layers of the vessel. The balloon may then be inflated to tear part of the arterial layer away and push the occlusion away. With the balloon catheter 10, 46 described herein, the balloon 12 may be positioned near the occluded region and inflated to anchor the balloon catheter 10, 46 in the vasculature. A compliant balloon 12 may be desirable in this application. A guide wire may then be inserted through the third lumen 20 and out the third opening 21 to extend the guide wire around the occlusion and through the arterial layers. The occlusion may then be treated in a conventional manner. An advantage of using the balloon catheter 10, 46 for this procedure is that the position of the third opening 21 is anchored in place when the guide wire is being pushed through the arterial layers. In addition, this method may be combined with any of the other methods described herein.

In another medical treatment, the balloon catheter 10, 46 may be used to treat a stenosis by determining the degree to which the vessel is occluded. In this method, the balloon catheter 10, 46 may be moved through the stenosis with the balloon 12 deflated so that the third opening 21 passes through the stenosed region. Pressure may then be measured at the third opening 21 as the third opening 21 moves through the stenosed region to determine the extent of occlusion of the region. Again, this method may be combined with other methods described herein. For example, after the physician has determined the degree of occlusion of the stenosed region, the physician can inflate the balloon 12 at the stenosed region to dilate the stenosed region without needing to insert a different device into the stenosis. Thus, the balloon 12 may remain substantially at the stenosed region throughout the procedure.

Figure 5:
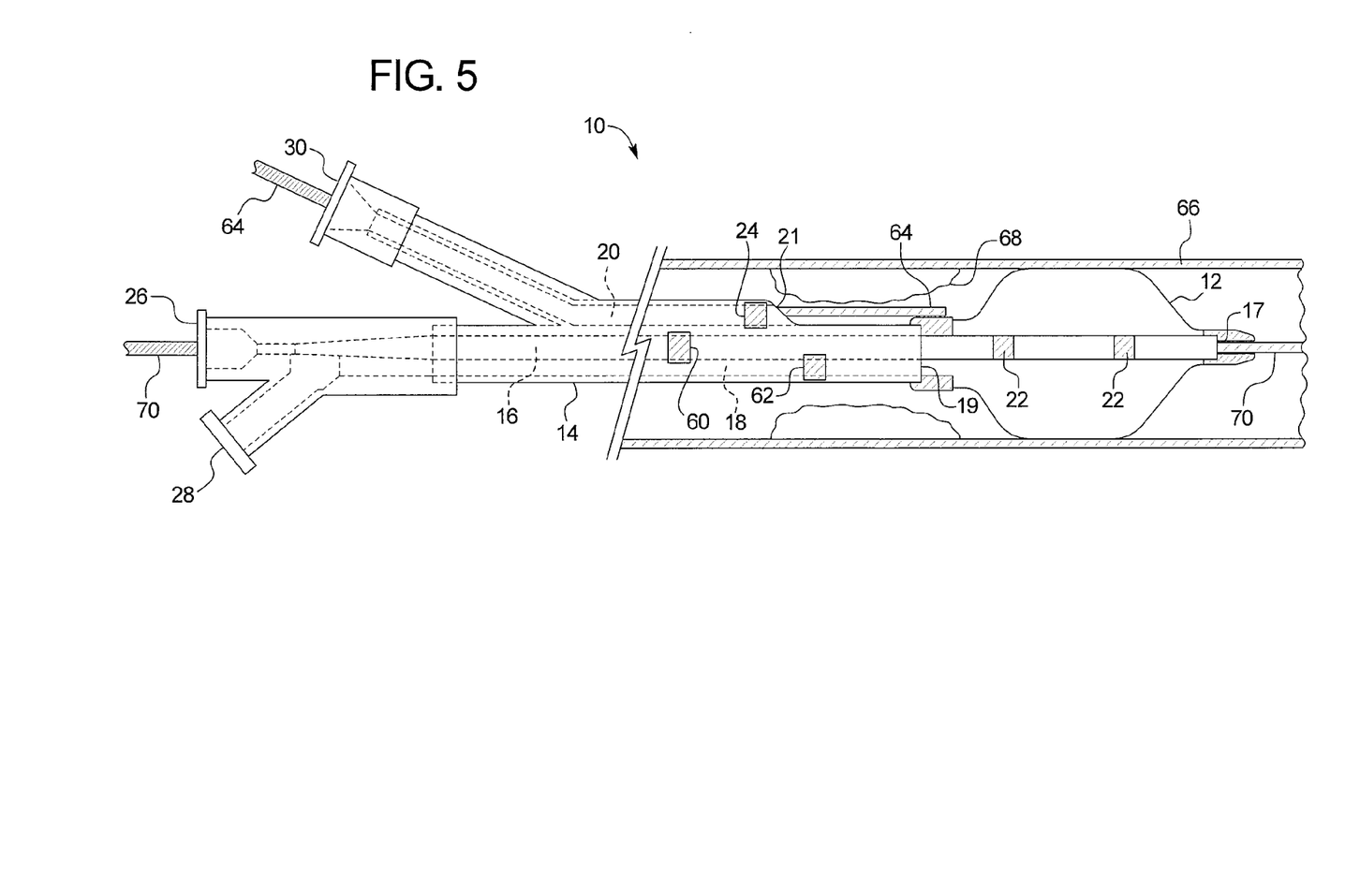
FIG. 5 is a side view of a medical procedure using the balloon catheter.

As shown in FIG. 5, the balloon catheter 10, 46 may also be used with a pressure wire 64 to determine the degree to which the vessel 66 is occluded. In a preferred use of the balloon catheter 10, 46 with the pressure wire 64, the balloon 12 may be positioned on one side of a stenosis 68, and the third opening 21 may be positioned on the other side of the stenosis 68. For example, the balloon 12 may be located on the downstream side and the third opening 21 may be located on the upstream side. In this application, it may be desirable for the third opening 21 and the balloon 12 to be spaced apart farther than described above to allow enough distance for the third opening 21 and balloon 12 to span the stenosis 68 and obtain the desired pressure readings. For example, it may be desirable in this instance for the third opening 21 to be about 200 mm to about 300 mm from the proximal end of the balloon 12.

The balloon 12 is preferably inflated against the vessel wall 66 with low-pressure to stabilize the balloon catheter 10, 46 in the vessel 66 without traumatizing the healthy, non-stenosed vessel wall 66. For example, a pressure of 3 atm. or less may be desirable. The pressure wire 64 may then be pushed out of the third opening 21 of the third lumen 20 and moved along the stenosed region 68 to take pressure readings along the length of the stenosis 68 to determine the degree of occlusion. This may be done before the balloon 12 is inflated within the stenosis 68 to dilate the stenosis 68, or after the stenosis 68 has been dilated, or before and after dilation. In particular, it is most desirable to initially push the pressure wire 64 through the stenosis 68 so that the end of the wire 64 is on the downstream side of the stenosis 68 adjacent the semi-inflated balloon 12. In this area, the pressure readings will typically be relatively low. Pressure readings are then taken with the pressure wire 64 as the pressure wire 64 is pulled back through the stenosis 68 until the end of the wire 64 is on the upstream side of the stenosis 68 adjacent the third opening 21 of the third lumen 20. If the stenosis 68 has a high degree of occlusion, the pressure readings will rise significantly as the pressure wire 64 moves through the stenosis 68, whereas the pressure readings will be more uniform if there is only a low degree of occlusion.

Thus, a physician can use pressure readings obtained from the pressure wire 64, or through the third lumen 20 as described above, to determine the type of treatment that is preferred. For example, a physician could use the pressure readings after dilation of the stenosis 68 to determine whether it is desirable to implant a stent through the stenosis 68 or whether stent implantation is unnecessary. An advantage of the pressure wire 64 method for obtaining pressure readings is that the balloon 12 can fix the balloon catheter 10, 46 longitudinally within the vessel 66. This allows improved control over the pressure wire 64 as it is moved through the stenosed region 68. Also, the pressure readings can be taken quickly without needing to change wires or devices during the procedure. For example, the guide wire 70 may be left in the first lumen 16 throughout the entire procedure without needing to remove the guide wire 70 and replace it with a pressure wire 64. In addition, the balloon catheter 10, 46 can be left in the vessel 66 during the procedure, and can be used as a guide for the pressure wire 64 and can be used to dilate the stenosis 68 before and/or after the pressure readings are obtained.

In another medical treatment, the balloon catheter 10, 46 may be used to treat a vessel with stem cells. In a conventional method of stem cell treatment, a guide wire and guide catheter are threaded to the distal end of a treatment site. The guide wire is then withdrawn from the patient's body to allow sufficient space to pump stem cells through the guide catheter lumen. Stem cells are then pumped through the guide catheter as the guide catheter is withdrawn through the treatment site so that the stem cells exit the distal end of the guide catheter along the entire length of the treatment site. The guide wire is then reinserted into the guide catheter, and the guide wire is threaded back to the distal end of the treatment site. The guide catheter is then withdrawn from the patient's body. Next, a conventional balloon catheter is threaded over the guide wire to the distal end of the treatment site and inflated. The balloon typically remains inflated for several minutes to prevent the stem cells from escaping the treatment site so that the stem cells engage the vessel wall. Once sufficient time has been allowed for the stem cells to be taken up by the vessel wall, the balloon is deflated and withdrawn from the patient's body. However, there are several disadvantages with this procedure. One significant disadvantage is that the treatment site must be retraversed with the guide wire after the stem cells have been injected. This can be difficult and time consuming. In addition, this can result in a significant amount of time passing between when the stem cells are injected and the balloon is inflated at the distal end of the treatment site. As a result, some of the stem cells may escape from the treatment site before the balloon is inflated due to blood flow through the vessel.

In the improved method of treatment, a guide wire is threaded to the distal end of the treatment site. The balloon catheter 10, 46 is then threaded over the guide wire to the proximal end of the treatment site. Stem cells are then pumped through the third lumen 20 so that the stem cells exit the third opening 21. While the stem cells are being pumped through the third lumen 20, the balloon catheter 10, 46 may be advanced through the treatment site so that the stem cells exit the third opening 21 along the entire length of the treatment site. Once the full length of the treatment site has been treated with stem cells, the balloon 12 is inflated adjacent the distal end of the treatment site. The balloon 12 remains inflated for several minutes to trap the stem cells in the treatment site and encourage uptake of the stem cells into the vessel wall. Once sufficient time has been allowed for the stem cells to be taken up by the vessel wall, the balloon 12 is deflated and the balloon catheter 10, 46 and the guide wire are withdrawn from the patient's body. Accordingly, the overall time of the procedure can be significantly reduced and there may be a reduced loss of stem cells due to blood flow through the treatment site. It is preferable in this method to use a compliant balloon 12 since the purpose of the balloon 12 is to obstruct the vessel lumen and not to dilate the vessel. In addition, it is preferable to use a liner 40 for the third lumen 20 that is lubricious, such as thermoset polyimide or PTFE, to minimize stress on the stem cells as they pass through the third lumen 20.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A balloon catheter for medical treatment, comprising:
   a catheter shaft comprising a first lumen, a second lumen and a third lumen, each of said first, second and third lumens being in communication with corresponding first, second and third ports, and at least said second and third ports being located at a proximal end of said catheter shaft, said third lumen being defined by a thin-walled liner made of a high strength material; and
   a balloon attached to a distal end of said catheter shaft, said first lumen extending through an inner cavity of said balloon to a first opening distal from said balloon, said first lumen thereby being adapted to receive a guide wire, said second lumen extending to a second opening within said inner cavity of said balloon, said second lumen thereby being adapted to communicate an inflation media to inflate and deflate said balloon, said third lumen extending to a third opening proximal from said balloon, said third lumen thereby being adapted to communicate with an exterior region around said catheter shaft proximal from said balloon;
   wherein said thin-walled liner is angled away from said first and second lumens near said proximal end of said catheter shaft, a proximal end of said thin-walled liner being bonded directly to a hub defining said third port.

2. The balloon catheter according to claim 1, wherein said thin-walled liner is made from thermoset polyimide.

3. The balloon catheter according to claim 1, wherein said thin-walled liner is made from etched PTFE.

4. The balloon catheter according to claim 1, wherein said first and second lumens are defined by thin-walled liners made of a high strength material.

5. The balloon catheter according to claim 1, further comprising a radiopaque marker adjacent said third opening.

6. The balloon catheter according to claim 5, wherein said radiopaque marker adjacent said third opening is a radiopaque band disposed around said third lumen, and further comprising a radiopaque band disposed around said first lumen and a radiopaque band disposed around said second lumen, one of said radiopaque bands of said first and second lumens being adjacent said radiopaque band of said third lumen and the other radiopaque band being adjacent the one radiopaque band or the radiopaque band of said third lumen.

7. The balloon catheter according to claim 1, wherein said third opening is located about 10 mm to about 50 mm from a proximal end of said balloon.

8. The balloon catheter according to claim 1, wherein said third opening is located about 5 mm to about 10 mm from a proximal end of said balloon.

9. The balloon catheter according to claim 1, wherein said third opening is located about 200 mm to about 300 mm from a proximal end of said balloon.

10. The balloon catheter according to claim 1, further comprising a braided reinforcement structure surrounding said first, second and third lumens between said proximal end of said catheter shaft and said third opening, and a thermoplastic layer surrounding said braided reinforcement structure.

11. A method of treating a patient, comprising:
    inserting a balloon catheter through a vessel, said balloon catheter comprising a catheter shaft comprising a first lumen, a second lumen and a third lumen, each of said first, second and third lumens being in communication with corresponding first, second and third ports, and at least said second and third ports being located at a proximal end of said catheter shaft, said third lumen being defined by a thin-walled liner made of a high strength material, and a balloon attached to a distal end of said catheter shaft, said first lumen extending through an inner cavity of said balloon to a first opening distal from said balloon, said first lumen thereby being adapted to receive a guide wire, said second lumen extending to a second opening within said inner cavity of said balloon, said second lumen thereby being adapted to communicate an inflation media to inflate and deflate said balloon, said third lumen extending to a third opening proximal from said balloon, said third lumen thereby being adapted to communicate with an exterior region around said catheter shaft proximal from said balloon, wherein a proximal portion of said thin-walled liner is angled away from said first and second lumens near said proximal end of said catheter shaft, a proximal end of said thin-walled liner being bonded directly to a hub defining said third port;

positioning said balloon near a treatment site in said vessel; and treating said treatment site through said third opening of said third lumen.

12. The method according to claim 11, wherein said treatment site is a stenosis, and further comprising inflating said balloon at said stenosis to dilate said stenosis and deflating said balloon at said stenosis after said inflation, wherein said treating comprises injecting contrast solution through said third lumen and out said third opening without substantially moving said balloon from said stenosis after deflating said balloon.

13. The method according to claim 12, further comprising inflating said balloon at said stenosis to dilate said stenosis a second time after injecting said contrast solution.

14. The method according to claim 11, wherein said treatment site is a stenosis, and further comprising inflating said balloon at said stenosis to dilate said stenosis and deflating said balloon at said stenosis after said inflation, wherein said treating comprises injecting a drug to treat a vessel spasm through said third lumen and out said third opening without substantially moving said balloon from said stenosis after deflating said balloon.

15. The method according to claim 11, wherein said treatment site is a stenosis, and further comprising inflating said balloon at said stenosis to dilate said stenosis and deflating said balloon at said stenosis after said inflation, wherein said treating comprises inserting a dilation wire through said third lumen and out said third opening to extend said dilation wire between said stenosis and said balloon without substantially moving said balloon from said stenosis after deflating said balloon, and further comprising inflating said balloon at said stenosis to dilate said stenosis a second time with said dilation wire between said stenosis and said balloon.

16. The method according to claim 11, wherein said treatment site is a aneurysm, and further comprising positioning said third opening adjacent said aneurysm and pushing an embolization coil through said third lumen and out said third opening into said aneurysm.

17. The method according to claim 16, wherein said balloon is inflated distally of said aneurysm and contrast solution is injected through said third lumen and out said third opening to retain said contrast solution in a region around said aneurysm before said embolization coil is pushed into said aneurysm, and pushing said embolization coil into said aneurysm while said balloon is inflated and said contrast solution is retained around said region.

18. The method according to claim 16, wherein said balloon is inflated adjacent said aneurysm after said embolization coil is pushed into said aneurysm to seat said embolization coil in said aneurysm.

19. The method according to claim 11, wherein said treatment site is a substantially occluded region, and further comprising inflating said balloon near said occluded region to anchor said catheter shaft, wherein said treating comprises inserting a guide wire through said third lumen and out said third opening to extend said guide wire through arterial layers of said vessel and around said occluded region.

20. The method according to claim 11, wherein said treatment site is a stenosis, and further comprising moving said third opening through said stenosis while said balloon is deflated, wherein said treating comprises measuring a pressure change at said third opening as the third opening is moved through said stenosis to determine a degree of occlusion.

21. The method according to claim 11, wherein said treatment site is a stenosis, and further comprising positioning said balloon on one side of said stenosis and said third opening on an opposite side of said stenosis, at least partially inflating said balloon to stabilize said balloon catheter, inserting a pressure wire through said third lumen and out said third opening, and moving said pressure wire through said stenosis while said balloon is at least partially inflated, wherein said treating comprises measuring a pressure change with said pressure wire as said pressure wire is moved through said stenosis to determine a degree of occlusion.

22. The method according to claim 11, wherein said treatment site is a vessel, and further comprising positioning said third opening of said third lumen adjacent a proximal end of said treatment site, injecting stem cells through said third lumen and out said third opening while moving said third opening through said treatment site, and inflating said balloon adjacent a distal end of said treatment site.

23. The balloon catheter according to claim 1, wherein a non-included angle between said proximal portion of said thin-walled liner and a distal portion of said thin-walled liner is 30° or less.

24. The balloon catheter according to claim 1, further comprising a reinforcement outer layer along said proximal portion of said thin-walled layer supporting said thin-walled liner.

25. The balloon catheter according to claim 24, wherein a non-included angle between said proximal portion of said thin-walled liner and a distal portion of said thin-walled liner is 30° or less, and said thin-walled liner is made from thermoset polyimide or etched PTFE.

26. The balloon catheter according to claim 25, further comprising a radiopaque marker adjacent said third opening, wherein said radiopaque marker adjacent said third opening is a radiopaque band disposed around said third lumen, and further comprising a radiopaque band disposed around said first lumen and a radiopaque band disposed around said second lumen, one of said radiopaque bands of said first and second lumens being adjacent said radiopaque band of said third lumen and the other radiopaque band being adjacent the one radiopaque band or the radiopaque band of said third lumen, and further comprising a braided reinforcement structure surrounding said first, second and third lumens between said proximal end of said catheter shaft and said third opening, and a thermoplastic layer surrounding said braided reinforcement structure.

* * * * *